(12) United States Patent
Renné

(10) Patent No.: US 11,846,641 B2
(45) Date of Patent: Dec. 19, 2023

(54) BINDING MOLECULE ACTIVATING FXII

(71) Applicant: Universitätsklinikum Hamburg-Eppendorf, Hamburg (DE)

(72) Inventor: Thomas Renné, Hamburg (DE)

(73) Assignee: Universitaetsklinikum Hamburg-Eppendorf, Hamburg (DE)

( * ) Notice: Subject to any disclaimer, the term of this patent is extended or adjusted under 35 U.S.C. 154(b) by 723 days.

(21) Appl. No.: 16/622,064

(22) PCT Filed: Jun. 28, 2018

(86) PCT No.: PCT/EP2018/067505
§ 371 (c)(1),
(2) Date: Dec. 12, 2019

(87) PCT Pub. No.: WO2019/002518
PCT Pub. Date: Jan. 3, 2019

(65) Prior Publication Data
US 2020/0182890 A1 Jun. 11, 2020

(30) Foreign Application Priority Data
Jun. 29, 2017 (EP) ..................................... 17178768

(51) Int. Cl.
C07K 16/36 (2006.01)
G01N 33/86 (2006.01)
G01N 33/68 (2006.01)

(52) U.S. Cl.
CPC ............. *G01N 33/86* (2013.01); *C07K 16/36* (2013.01); *G01N 33/6854* (2013.01); *C07K 2317/75* (2013.01)

(58) Field of Classification Search
None
See application file for complete search history.

(56) References Cited

FOREIGN PATENT DOCUMENTS

WO 2014089493 6/2014

OTHER PUBLICATIONS

Zhu et al., Thromb Res. Dec. 2014;134(6):1335-43. doi: 10.1016/j.thromres.2014.09.030. Epub Oct. 2, 2014. PMID: 25303860.*
Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Citarella et al., (1992) "Control of human coagulation by recombinant serine proteases Blood clotting is activated by recombinant factor XI1 deleted of five regulatory domains", Eur J Biochem, 208:23-30.
Citarella et al., (1996) "Structure/function analysis of human factor XII using recombinant deletion mutants Evidence for an additional region involved in the binding to negatively charged surfaces", Eur J Biochem, 238:240-249.
Clarke et al., (1989) "Mapping of a Putative Surface-binding Site of Human Coagulation Factor XII*", J Biol Chem 264(19):11497-11502.
De Maat et al., (2016) "Factor XII: form determines function", Journal of Thrombosis and Haemostasis, 14 (8):1498-1506.
Herwald et al., "Activation of the contact-phase system on bacterial surfaces—a clue to serious complications in infectious diseases", Nature Medi. Nature Pub. Co, 4(3):298-302.
Johne (2008) "Pathologische Aktivierung des Gerinnungsfaktors XII—Heparin-Protamin-Komplikationen Inaugural—Dissertation zur Erlangung der DoktorwUrde der Medizinischen Fakultat der Julius-Maximilians-Universitat Wurzburg vorgelegt von", Universitat Wurzburg, 1-69.
Labberton (2016) "Mechanisms and regulation of the polyphosphate/factor XII-driven contact system in thrombosis and hemostasis", The Department of Molecular Medicine and Surgery, 1-68.
Larsson et al., (2014) "A Factor XIIa Inhibitory Antibody Provides Thromboprotection in Extracorporeal Circulation Without Increasing Bleeding Risk", Sci Transl Med, 6:222, 222ra17.
Muller (2009) "Analysis of the factor XII—driven contact system activation in vivo", Universitat Wurzburg, 1-83.
Nuijens et al., (1989) "Activation of the Contact System of Coagulation by a Monoclonal Antibody Directed Against a Neodeterminant in the Heavy Chain Region of Human Coagulation Factor XI1 (Hageman Factor)*", J Biol Chem, 264 (22):12941-12949.
Pixley et al., (1987) "A Monoclonal Antibody Recognizing an Icosapeptide Sequence in the Heavy Chain of Human Factor XII Inhibits Surface—catalyzed Activation", J Biol Chem, 262(21):10140-10145.
Ravon et al., (1995) "Monoclonal Antibody F1 Binds to the Kringle Domain of Factor XI1 and Induces Enhanced Susceptibility for Cleavage by Kallikrein", Blood, 86(11): 4134-4143.
Saito et al., (1985) "Production and Characterization of a Murine Monoclonal Antibody Against a Heavy Chain of Hageman Factor (Factor XII)" Blood, 65(5):1263-1268.
Vazquez-Lombardi et al., (2015) "Challenges and opportunities for non-antibody scaffold drugs", Drug Discovery Today, 20(10):1271-1283.

(Continued)

*Primary Examiner* — Michael Szperka
(74) *Attorney, Agent, or Firm* — Stephan A. Pendorf; Patent Central LLC

(57) ABSTRACT

The present invention relates to a binding molecule, in particular an antibody or binding fragment thereof, capable of activating FXII, which binds to the proline rich domain of FXII. In particular, the invention is directed to FXII activating antibodies or binding fragments thereof which binds to the proline rich domain of FXII. The invention also encompasses the use of the binding molecule directed to the proline rich domain of FXII as blood coagulation activator, e.g. in diagnostic blood coagulation tests. Corresponding methods and blood coagulation test are also encompassed.

Figure 1:
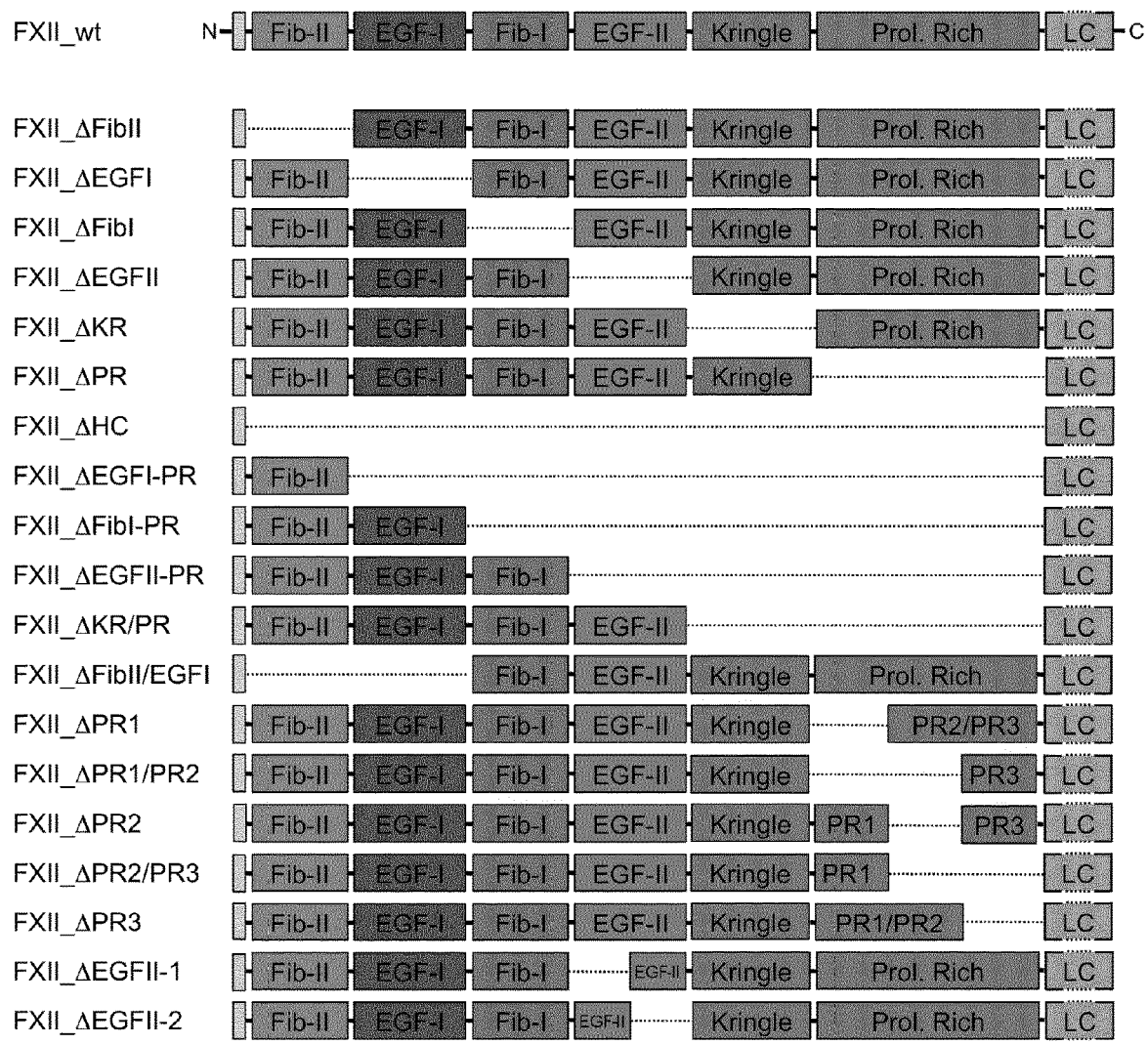

2 Claims, 8 Drawing Sheets
Specification includes a Sequence Listing.

(56) References Cited

OTHER PUBLICATIONS

Tabarzad, Maryam and Jafari, Marzieh, (2016) "Trends in the Design and Development of Specific Aptamers Against Peptides and Proteins", Protein J., 35:81-99.
Heestermans et al., (2021) "Identification of the factor XII contact activation site enables sensitive coagulation diagnostics", Nature Communications, 5596:1-17.
Li et al., (2014) "Development of Aptamer oligonucleotides as Anticoagulants and Antithrombotics for Cardiovascular Diseases: Current Status", Thrombosis Research, 134:769-773.
Woodruff et al., (2013) "Inhibiting the intrinsic pathway of coagulation with a FXIItargeting RNA Aptamer", Thromb Haemost., 11(7):1-17.

* cited by examiner

Clone 37

BINDING MOLECULE ACTIVATING FXII

FIELD OF THE INVENTION

The present invention relates to a binding molecule, in particular an antibody or binding fragment thereof, capable of activating FXII, which binds to the proline rich domain of FXII. In particular, the invention is directed to FXII activating antibodies or binding fragments thereof which bind to the proline rich domain of FXII. The invention also encompasses the use of the binding molecule directed to the proline rich domain of FXII as blood coagulation activator, e.g. in diagnostic blood coagulation tests. Corresponding methods and blood coagulation tests are also encompassed.

BACKGROUND OF THE INVENTION

Coagulation factor XII (FXII, Hageman factor) is of crucial importance for fibrin formation in vitro. FXII auto-activation induced by contact with negatively-charged surfaces is the principal mechanism for initiating the contact system and the "intrinsic" pathway of the coagulation cascade. Formed active serine protease FXIIa also triggers liberation of proinflammatory mediator bradykinin. In these pathways FXIIa activates its downstream targets, including factor XI (FXI) and plasma pre-kallikrein, respectively. Experimental animal models and patient studies have revealed that the FXIIa-driven contact pathway of coagulation critically contributes to thrombosis.

FXII zymogen protein (EC:3.4.21.38) is composed of a heavy chain followed by the a catalytic light chain. The heavy chain is constituted of six domains: (i) fibronectin type-II domain (Fib-II), (ii) an epidermal growth factor like domain (EGF-I), (iii) a fibronectin type-I domain (Fib-I), (iv) a second EGF-like domain (EGF-II), (v) a kringle domain, (vi) and a unique proline-rich domain. These domains mediate contact to other proteins and negatively charged surfaces. Despite the central role of FXII auto-activation in the process that initiates coagulation and inflammation, the FXII sequence that mediates contact to charged surfaces leading to FXII zymogen "contact activation" has remained illusive. Several studies over the last 30 years aimed to elucidate which specific domains of the FXII heavy chain participate in the surface binding-driven contact activation. These studies used domain deletion mutants and antibodies. Monoclonal antibody studies have highlighted multiple non-overlapping sites localised in FXII Fib-I, Fib-II and kringle domain that mediate interaction to contact activators such as kaolin (Clarke et al., 1989; Nuijens et al., 1989; Pixley et al., 1987; Rayon et al., 1995; Saito et al., 1985). Moreover, mutants used to analyze the mechanisms of FXII contact activation indicated that heavy chain sequences in the EGF-II, kringle and proline-rich domain, contribute to surface ("contact") binding (Citarella et al., 1992; Citarella et al., 1996). The identified FXII surface binding sites were partially contradictory and their in vivo relevance has remained unknown. Taken together, previous studies have led to non-consistent partially conflicting results and the FXII site(s) responsible for inducing contact activation has/have remained enigmatic. However, the absence of FXII heavy chain impairs contact activation indicating that the FXII surface-binding site is in its heavy chain.

Contact activation of FXII is the key step in blood coagulation tests that are frequently used. In particular, the FXII-based activated partial thromboplastin time (aPPT) diagnostic assay is used worldwide as diagnostic tool to assess integrity of the plasmatic coagulation system. This test is also commonly used to monitor anticoagulation therapy including heparin application, coagulation disorders including lupus anticoagulans/anti-phospholipid syndrome or factor deficiencies in patients. In this test, blood coagulation is started by addition of negatively charged surfaces, such as silicate beads, binding to FXII and thereby triggering its auto-activation. Negatively charged surfaces are however disadvantageous, since the activation of FXII is rather poorly defined. FXII interactions with the negatively charged surfaces depend on the size and the features of the surfaces. Further, antibodies or lipids and other molecules that are present in the plasma sample frequently bind to the negatively charged surfaces and thereby interfere with the contact activation activity of these charged surfaces, thereby modulating the extent of the contact activation. Hence, the contact activation of FXII by negatively charged surfaces cannot be precisely controlled. Therefore, there is a need for improved activation of FXII that (1) proceeds in solution and (2) can be precisely controlled by specific interaction with the relevant contact activation domain that allows for a defined ideally stoichiometric activation of FXII.

OBJECTIVES AND SUMMARY OF THE INVENTION

The application describes the identification of the proline rich domain of FXII as site, which mediates the contact activation. In particular, it was found that a continuous segment in the C-terminal part of the proline rich domain mediates activation of human FXII by binding to negatively charged surfaces. Further, experimental data proofs that specific binding of a binding molecule to this domain activates FXII.

Hence a first aspect of the invention relates to a binding molecule capable of activating FXII, wherein the binding molecule is capable of binding to the proline rich domain of FXII defined by the amino acid sequence set forth in SEQ ID NO: 1.

Particularly, the binding molecule is capable of binding to the C-terminal part of the proline rich domain of FXII defined by the amino acid sequence set forth in SEQ ID NO: 2. More particularly, the binding molecule is capable of binding the C-terminal part of the proline rich domain of FXII defined by the amino acid sequence set forth in SEQ ID NO: 3. Even more particularly, binding molecule is capable of binding the C-terminal part of the proline rich domain of FXII defined by the amino acid sequence set forth in SEQ ID NO: 4.

In some embodiments, the binding molecule is an antibody or a binding fragment thereof.

Typically, the binding molecule stoichiometrically binds to FXII, e.g. in a defined ratio.

Preferably the binding molecule is present in solution. Thus the binding molecule is not present in dispersion.

The binding molecule may activate blood coagulation and/or inflammation via bradykinin or other FXIIa-driven reactions.

Therefore, another aspect of the invention refers to the use of the binding molecule defined in any one of the preceding claims as blood coagulation activator. For example, the binding molecule is used in a blood coagulation test. Usually the blood coagulation test is a (activated) partial thromboplastin time or thrombin generation assay.

Thus another aspect of the invention refers to a blood coagulation test comprising the following steps:

(a) contacting a sample containing citrate plasma with a binding molecule as defined herein, (b) adding calcium to the sample of step (a), (c) measuring of the coagulation time or the concentration of molecules formed upon activation of FXII within the sample of step (b).

Another aspect of the invention refers to a method for activating FXII, comprising contacting a FXII comprising sample with the binding molecule as defined herein. In a specific embodiment, the FXII comprising sample is further contacted with other contact activators such as the inorganic polyanionic polymers, such as polyphosphate.

The invention further relates to a kit comprising a binding molecule as defined herein and at least one of the following:
  at least one binding molecule as described herein
  buffer
  further contact activator, such as polyphosphate,
  sodium citrate,
  FXIIa,
  chromogenic or fluorogenic substrate,
  phospholipids,
  instructions for use.

FIGURE LEGENDS

FIG. 1: Schematic of full-length FXII (FXII_wt) and FXII deletion mutants. The heavy chain is constituted of six domains: (i) fibronectin type-II domain (Fib-II), (ii) an epidermal growth factor like domain (EGF-I), (iii) a fibronectin type-I domain (Fib-I), (iv) a second EGF-like domain (EGF-II), (v) a kringle domain (Kringle), (vi) and a unique proline-rich domain (Prol. Rich). The catalytic light chain is abbreviated by LC.

Figure 2:
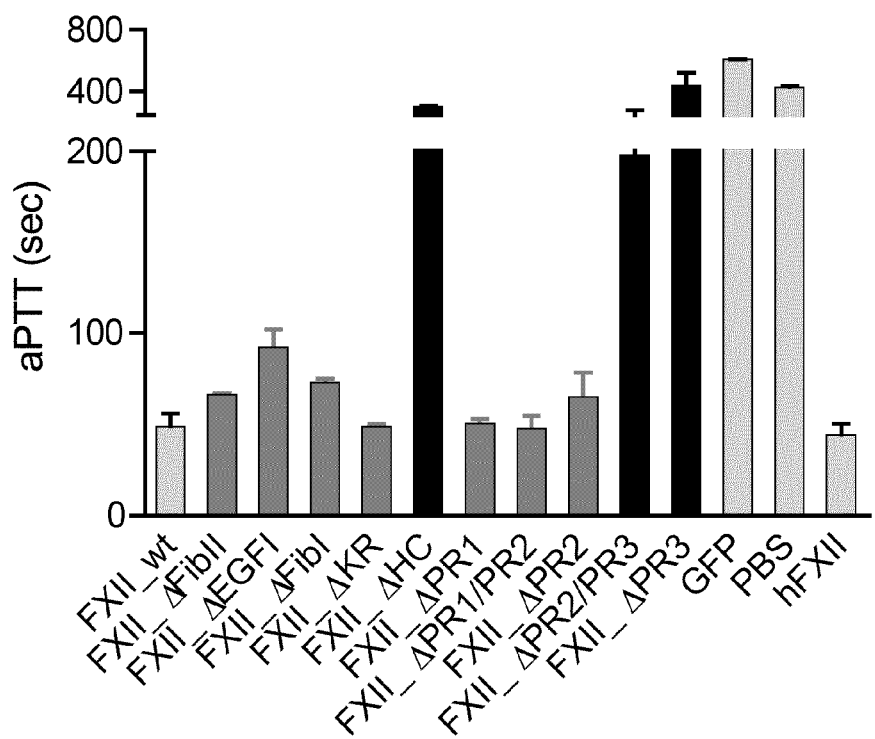

FIG. 2: Clotting assay of human FXII deficient plasma reconstituted with FXII-wt or deletion mutants. Activated partial thromboplastin time (aPTT) was determined by adding FXII deficient plasma reconstituted with full length FXII (FXII_wt) or FXII deletion mutants. As controls, FXII deficient plasma was reconstituted with purified human FXII from plasma (positive control) or supernatant from cell transfected with control green fluorescent protein (GFP) or PBS buffer (negative controls). The mutants are depicted in FIG. 1.

Figure 3:
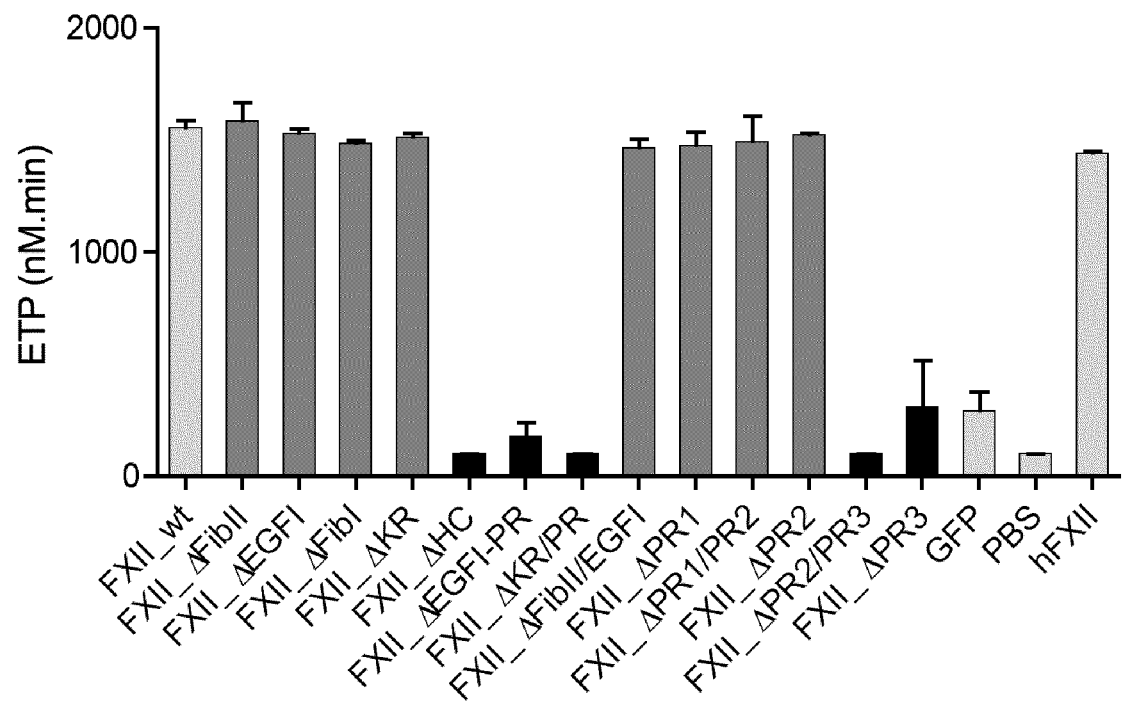

FIG. 3: Thrombin formation in human FXII deficient plasma reconstituted with FXII_wt or deletion mutants. Endogenous Thrombin potential (ETP) in real time. Coagulation was stimulated by adding kaolin to FXII deficient plasma reconstituted with full length FXII (FXII_wt) or FXII deletion mutants from concentrated supernatant of cells, in presence of phospholipids, calcium and a fluorogenic substrate. As controls, FXII deficient plasma was reconstituted with purified human FXII (hFXII) (positive control) or supernatant from cell transfected with GFP or PBS buffer (negative controls). The mutants are depicted in FIG. 1.

FIG. 4: Polyclonal antibody targeting the C-terminal portion of the FXII proline-rich domain induces FXII-mediated coagulation in plasma (anti-PR3). FIG. 4A: Western Blot analysis with the polyclonal anti-PR3 antibody (against the C-terminal portion of the proline-rich domain; GALPAKREQPPSLT sequence (SEQ ID NO:4) in panel A). Anti-PR3 recognizes full size FXII in normal human plasma, plasma purified human FXII (hFXII), and recombinant expressed normal FXII (FXII_wt) but not the FXII_ΔPR3 mutant lacking the C-terminal portion of the proline rich domain. A polyclonal anti-FXII antibody is used to confirm equal loading per lane. FIG. 4B: Antibody anti-PR3 activates human FXII. Anti-PR3 was incubated with purified FXII (hFXII) and the development of FXIIa enzymatic activity was analysed photometrically using the chromogenic substrate S-2302. As controls, hFXII was incubated with kaolin (positive control of FXII contact activation, Ctrl.+) or with an antibody directed against a bacterial protein unrelated to plasma proteins (negative control for effect specificity to FXII, anti-PPX, Ctrl. FIG. 4C: FXII activity assessed by conversion of the chromogenic substrate S-2302 in pooled normal human plasma supplemented with PBS, Kaolin, anti-PR3 polyclonal antibody, or an unrelated control antibody. FIG. 4D: Antibody anti-PR3 enhances contact activation by the FXII natural activator polyphosphate. After pre-incubation of purified FXII (hFXII) with anti-PR3, the activator polyphosphate (P30) was added and its enzymatic activity was analysed. As negative control, hFXII was pre-incubated with anti-PPX antibody. FIG. 4E: aPTT clotting times in normal pooled plasma supplemented with buffer, polyP, anti-Vasodilator-stimulated phosphoprotein (control) antibody or combinations of polyP and anti-PR3 followed by recalcification, n=3. FIG. 4F: Real time thrombin formation (CAT, ETP assay) in normal pooled plasma spiked with polyP30, anti-PR3, and control antibody (anti-dsDNA). 150 nM FXII in the reaction mixture. Ratios represent the molar ratio of antibody to FXII protein in the mixture. Means of n=3.

FIG. 5 Monoclonal anti-FXII antibody raised against the C-terminal portion of the proline rich domain activates FXII and induces plasma coagulation. FIG. 5A: Analysis of the monoclonal antibody raised against the GALPAKREQPPSLT peptide (SEQ ID NO:4) in the C-terminal portion of the proline rich domain for binding to FXII and produced by the hybridoma cell line HFXII 37-4-1. ELISA plates were coated with human FXII zymogen (50 μl/well at 2 m/ml), incubated with hybridoma cell supernatants or hyperimmune serum of GALPAKREQPPSLT (SEQ ID NO:4)-immunized (antiserum) or control mice (negative control) and bound antibody was quantified using a goat anti-mouse IgG Fc-specific secondary antibody and substrate reaction. Absorbance at 405 nm after 15 min incubation is blotted, n=2. FIG. 5B: Antibody secreted by anti-GALPAKREQPPSLT (SEQ ID NO: 4) hybridoma clone HFXII 37-4-1 (clone 37) was analysed for FXII expression by Western blotting. 1 ul and 0.3 ul FXII-deficient plasma was loaded in lanes 1 and 2, respectively, followed by normal human pool plasma (0.3 ul) in lane 3. Antibody derived from hybridoma HFXII 37-4-1 detected FXII at 70 kDa. FIG. 5C: Monoclonal antibody produced by hybridoma clone HFXII 37-4-1 (clone 37) induced FXII activity determined by conversion of chromogenic substrate S-2302 in pooled human plasma (diluted to 180 nM FXII). Antibody was inactive to induce S-2302 conversion in FXII deficient plasma (no detectable FXII in Western blot). Plasma was incubated with PBS buffer or antibody at 187 nM and analysed at 3 hours, average of n=2 is shown. FIG. 5D: Real time thrombin formation (CAT, ETP assay) in normal pooled plasma spiked with polyP30, and antibody purified from hybridoma HFXII 37-4-1 (clone 37). FXII concentration in the mixture is 150 nM. Ratios represent the molar ratio of antibody to FXII protein.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense. If a specific meaning is conveyed to certain terms, definitions of terms will be given in the following in the context of which the terms are used.

A first aspect of the invention relates to a binding molecule capable of activating FXII, wherein the binding molecule is capable of binding to the proline rich domain of FXII defined by the amino acid sequence set forth in SEQ ID NO: 1.

The term "capable of activating FXII" refers to the capability of initiating formation of the enzymatic activity of FXII zymogen, leading to activated FXII, i.e. the serine protease FXIIa. Conversion of the zymogen to the active enzyme is initiated by the binding molecule. The capability of the binding molecule to activate FXII may be measured by a chromogenic substrate assay, e.g. using the chromogenic substrate S-2302 (Chromogenix, Sweden). Thereby the absorbance at 405 nm is measured in the presence of FXII, the chromogenic substrate and the binding molecule. As positive control a sample comprising FXII and kaolin could be used. As negative control a sample containing FXII without a FXII binding molecule or specific FXIIa inhibitors may be used. The increase of the absorbance indicates that the binding molecule activates FXII. Absorbance of more than 0.5, preferably more than 0.75, more preferably 1.0, most preferably 1.5 over background level typically indicates that the binding molecule is capable of activating FXII.

"Factor XII" or "FXII" refers to the factor XII zymogen protein (EC:3.4.21.38; Uniprot: P00748). The protein is composed of a heavy chain followed by a catalytic light chain. The heavy chain is constituted of six domains: (i) fibronectin type-II domain (Fib-II), (ii) an epidermal growth factor like domain (EGF-I), (iii) a fibronectin type-I domain (Fib-I), (iv) a second EGF-like domain (EGF-II), (v) a kringle domain, (vi) and a unique proline-rich domain. By contact activation the zymogen FXII is converted to the serine protease factor XIIa.

The amino acid sequence of the proline-rich domain is set forth in SEQ ID NO: 1.

The term "capable of binding" refers to a molecule that binds to the proline rich domain of FXII with a $K_D$ that is at least twofold less than its $K_D$ for binding to other proteins (e.g., BSA, casein, or any other specified polypeptide, in particular polypeptide that does not contain the proline rich sequence of FXII as defined herein). Typically, the antibody binds with a dissociation constant ($K_D$) of $10^{-6}$ M, preferably $10^{-7}$ M or less. In particular, with regard to antibodies the term "capable of binding" refers to antibody binding to a predetermined antigen. Typically, the antibody binds to the predetermined antigen with a $K_D$ that is at least twofold less than its $K_D$ for binding to a nonspecific antigen (e.g., BSA, casein, or any other specified polypeptide) other than the predetermined antigen.

Binding of an antibody to the proline rich domain of FXII, in particular the C-terminal part of the proline rich domain of FXII may be tested by a western blot assay. In particular, different versions of FXII, that differ in the presence or absence of different domains or parts thereof in a western blot assay may be used for determination whether the binding molecule binds to FXII and to which domain or part of domain it is binding.

Typically, the binding molecule is capable of binding to the C-terminal part of the proline rich domain of FXII defined by the amino acid sequence set forth in SEQ ID NO: 2. In particular the binding molecule is capable of binding the C-terminal part of the proline rich domain of FXII defined by the amino acid sequence set forth in SEQ ID NO: 3. More particular, the binding molecule is capable of binding the C-terminal part of the proline rich domain of FXII defined by the amino acid sequence set forth in SEQ ID NO: 4.

In some embodiments the binding molecule stoichiometrically binds to FXII. That means that there is a distinct ratio of binding molecule and FXII. If one binding molecule binds to one FXII molecule the stoichiometry is 1:1. The stoichiometry of binding molecule to FXII may range from 10:1 to 1:10, preferably 3:1 to 1: 3, more preferably 2:1 to 1:2, most preferably 1:1. The stoichiometry may be determined e.g. by plasmon resonance biosensor technology.

In some embodiments, the binding molecule is present in solution that means that the binding molecule is not present in dispersion. In particular the binding molecule is not present in a colloidal dispersion. Known activators of FXII such as kaolin beads or micronized silica are present in dispersion. Dispersions can be differentiated from solutions by the Tyndall effect, i.e. the scattering of light as a light beam passes through a dispersion.

The binding molecule may activate blood coagulation. By the binding of the binding molecule to the proline rich domain of FXII, in particular to the C-terminal part of the proline rich domain of FXII, as defined herein, FXII undergoes a conformational change to the activated FXIIa serine protease. Thereby the clotting cascaded is triggered which leads inter alia via the activation of factor XI (FXI) to thrombin formation and ultimately to the generation of fibrin polymers. Hence by the binding of the binding molecule to FXII triggers fibrin clot formation in plasma in vitro and fibrin formation can be measured e.g. photometrically, by turbidity or mechanically.

The binding molecule of the present invention therefore enhances FXII contact activation. That means that the binding molecule may be used to enhance contact activation of unspecific activators, such as polyphosphate.

Typically, the binding molecules of the invention maintain the activation of FXII. That means that after activation of FXII it stays in its active form FXIIa and does not rapidly lose its activity.

In a specific embodiment, the binding molecule is an antibody or a binding fragment thereof.

The term "binding molecule" includes not only antibodies and binding fragments thereof but also includes other molecules, such as non-antibody protein scaffold proteins (Vazquez-Lombardi R. et al., 2015), aptameres, nucleotide based molecules, and small molecules.

Antibodies can be differentiated into five main classes on the basis of their heavy chain, the IgM (μ), IgD (δ), IgG (γ), IgA (α) and IgE (ε) antibodies, IgG antibodies making up the largest proportion. Immunoglobulins can moreover be differentiated into the isotypes κ and λ on the basis of their light chains.

In spite of their different specificity, antibodies are structurally quite similar in construction. Thus, IgG antibodies typically are built up by two identical light and two heavy protein chains which are bonded to one another via disulfide bridges. The light chain comprises the N-terminal variable domain VL and the C-terminal constant domain CL. The heavy chain of an IgG antibody can be divided into an N-terminal variable domain VH and three constant domains CH1, CH2 and CH3. While the amino acid sequence is largely the same in the region of the constant domains, wide differences in sequence are typically found within the variable domains.

The person skilled in the art knows that each variable domain (the heavy chain VH and light chain VL) of an antibody comprises three hypervariable regions, sometimes called complementarity determining regions or "CDRs" flanked by four relatively conserved framework regions or "FRs" and refer to the amino acid residues of an antibody which are responsible for antigen-binding.

Binding fragments may include portions of an intact full length antibody, such as an antigen binding or variable region of the complete antibody. Examples of antibody fragments include F(ab'), F(ab')2, F(ab)c, and Fv fragments; diabodies; linear antibodies; single-Fv fragments (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), binding-domain immunoglobulin fusion proteins; camelized antibodies; VHH containing antibodies; chimeric antigen receptor (CAR); and any other polypeptides formed from antibody fragments. The skilled person is aware that the antigen-binding function of an antibody can be performed by fragments of a full-length antibody. The binding fragment may have a length of at least 5, at least 8, at least 10, at least 11, at least 12, at least 13, at least 14, at least 15 or more amino acids. The fragment may have the antigen-binding function of the antibody.

A Fab fragment consists of the $V_L$, $V_H$, $C_L$ and $C_H1$ domains. An F(ab')2 fragment comprises two Fab fragments linked by a disulfide bridge at the hinge region. An Fd is the $V_H$ and $C_H1$ domains of a single arm of an antibody. An Fv fragment is the $V_L$ and $V_H$ domains of a single arm of an antibody. An F(ab')c fragment comprises two F(ab') fragments plus part of the Fc domain. It is generated e.g. by plasmin digestion.

Binding fragments also encompass monovalent or multivalent, or monomeric or multimeric (e.g. tetrameric), CDR-derived binding domains.

The antibody may be a polyclonal or monoclonal antibody, preferably a monoclonal antibody. Typically the antibody is a recombinant antibody.

Consequently, preferred embodiments refer to an antibody or binding fragment thereof capable of activating FXII, wherein the antibody or binding fragment thereof is capable of binding to the proline rich domain of FXII defined by the amino acid sequence set forth in SEQ ID NO: 1.

Particular embodiments refer to an antibody or binding fragment thereof capable of activating FXII, wherein the antibody or binding fragment thereof is capable of binding the C-terminal part of the proline rich domain of FXII defined by the amino acid sequence set forth in SEQ ID NO: 2, in particular defined by the amino acid sequence set forth in SEQ ID NO: 3, more particularly defined by the amino acid sequence set forth in SEQ ID NO: 4.

Preferred embodiments refer to an antibody or binding fragment thereof capable of activating FXII, wherein the antibody or binding fragment thereof is capable of binding the C-terminal part of the proline rich domain of FXII defined by the amino acid sequence set forth in SEQ ID NO: 3.

In another specific embodiment of the invention, the antibody is generated by the immunization of the host animal, in particular with peptide, e.g. the sequence set out in SEQ ID NOs: 1 to 4, in particular set out in SEQ ID NO: 4, eliciting an immune response, followed by collection of the host serum and recovery of polyclonal antibodies, followed by the selection process wherein antibodies are selected by their ability to activate FXII, measured by conversion of chromogenic substrate S-2302 in pooled human plasma and decreased time to thrombin formation or clot formation as compared to a control antibody. The generation of polyclonal antibodies is both well known and well described in the art.

In yet another specific embodiment of the invention, the antibody is generated by the immunization of the host animal in particular with peptide, e.g. the sequence set out in SEQ ID NOs: 1 to 4, in particular set out in SEQ ID NO: 4, eliciting an immune response, followed by lymphocyte harvest and immortalization, creation of hybridoma, selection of true hybridoma, followed by screening for monoclonal clones, followed by the selection process wherein antibodies are selected by its ability to activate FXII, measured by conversion of chromogenic substrate S-2302 in pooled human plasma and decreased time to thrombin formation as compared to a control antibody. The generation of monoclonal antibodies is both well known and well described in the art.

In a specific embodiment, the antibody is produced by the hybridoma HFXII 37-4-1.

In a further embodiment, the antibody is 80% identical, preferably 90% identical, more preferred 95% identical to the antibody produced by the hybridoma HFXII 37-4-1.

In particular, the amino acid sequence of the antibody is 80% identical, preferably 90% identical, more preferred 95% identical to the amino acid sequence of the antibody produced by the hybridoma HFXII 37-4-1.

Another aspect of the invention refers to the use of the binding molecule as defined herein as blood coagulation activator. In particular, the invention refers to the use of the binding molecule defined herein as activator of the intrinsic blood coagulation. Specific embodiments refer to the use of an antibody as defined herein as activator of the intrinsic blood coagulation.

"Intrinsic blood coagulation" is initiated by the FXIIa-driven contact activation pathway. This pathway begins with the conversion of FXII zymogen to the serine protease FXIIa, which in turn activates FXI to FXIa. Activated FXII initiates the proinflammatroy kallikrein-kinin system and the intrinsic coagulation pathway, leading to the formation of bradykinin and thrombin, respectively. While bradykinin induces inflammation the intrinsic coagulation pathway ultimately leads to the formation of fibrin polymers.

In particular, the present invention refers to binding molecule as defined herein as activator of the blood coagulation in vitro, more particularly as activator of the intrinsic blood coagulation in vitro.

In specific embodiments, the binding molecule is used in a blood coagulation test. Preferably, the binding molecule is one of the antibodies as defined herein. Typically, the blood coagulation test is an in vitro blood coagulation test. The blood coagulation test may be diagnostic.

The blood coagulation test may determine the activated partial thromboplastin time (aPPT).

The aPPT test may be carried out as follows: In the presence or absence of phospholipids (e.g. cephalin contact activator, i.e. the binding molecule, in particular one of the antibodies as defined herein, of the present invention, is added to citrated plasma. Next, calcium is added. With the addition of calcium the time measurement begins and the clotting is initiated. The aPTT is the time taken from the addition of calcium to the formation of a fibrin clot. Typically, aPTT is measured in an automatic manner wherein clot formation is deemed to have occurred when the optical density of the mixture has exceeded a certain threshold, since the clot formation makes the mixture more opaque. Typically, the test is carried out at 37° C. and all solutions as well as citrated plasma are pre-warmed to 37° C.

Thus the invention relates to a blood coagulation test comprising the following steps:
    contacting a sample containing plasma with binding molecule as defined herein,
    measuring of the coagulation time of the sample containing plasma.

Blood coagulation is a highly elaborate, multi-step process, wherein thrombin formation, which is involved in the process of fibrin formation, is one of the prerequisites of blood coagulation.

In a specific embodiment of the invention, a binding molecule, such as the antibodies as defined herein, is used to determine the time to thrombin formation, which is decreased while the amount of the produced thrombin is increased, compared to the control antibody. In a specific embodiment, the blood coagulation test may comprise the following steps:
    (a) contacting a sample containing citrate plasma with a binding molecule, wherein the binding molecule is preferably an antibody or binding fragment thereof as defined herein,
    (b) adding calcium to the sample of step (a),
    (c) measuring of the coagulation time or the concentration of molecules formed upon the activation of FXII of the sample of step (b).

The term "molecules formed upon activation of FXII", includes FXIIa, and downstream effectors produced by FXIIa within the coagulation cascade, the bradykinin-forming pathway and the complement system. Downstream molecules of produced by FXIIa of the coagulation cascade include FXIa, FIXa, FXa, thrombin and fibrin, preferably FXIa and thrombin.

In another aspect of the invention, the binding molecule as described herein, in particular the antibody as described herein, can be used to quantify the activity of inhibitors of FXIIa or the activity of inhibitors of downstream effectors of FXIIa such as FXIa. Thus, the invention also encompasses the use of the binding molecule as described herein, in particular the antibody as described herein, for in in vitro measurement of the potency of FXII inhibitors or inhibitors of molecules downstream of FXII. For example, the activation of FXII by the binding molecule triggers the activation of FXI, which in turn leads to the initiation of coagulation via the intrinsic pathway. Hence, the activity of an inhibitor of FXIIa and/or FXIa can be quantified using the binding molecule according to the invention, due to the dependency of activation of FXI by a precisely defined amount of formed FXIIa.

In another example, the inactive precursor plasma prekallikrein is proteolytically cleaved by FXIIa, which in turn was activated by the binding molecule and therefore, activated and turned into kallikrein by FXIIa. Thus, the activity of an inhibitor of kallikrein can be quantified using the binding molecule according to the invention, due to dependency of activation of kallikrein on by a precisely defined amount of formed FXIIa.

In yet another embodiment, the antibody is used in aPPT-like tests which in turn is used to monitor heparin therapy in vitro. Furthermore the antibody is used in aPTT-like assays to assess coagulation factor levels and coagulation disorders especially lupus anticoagulans/antiphospho lipid syndrome.

Blood coagulation assays of the state of the art depend on contact activation by FXII. In particular, the aPPT assay is used as a diagnostic tool to assess the plasmatic coagulation system. In this test, blood coagulation is initiated by addition of negatively charged surfaces, e.g. silicate beads, binding to FXII and thereby triggering its auto-activation. Given the activation of FXII by negatively charged surfaces is rather poorly defined and highly dependent on the characteristics of the negatively charged surfaces as well as undesired interactions with plasma components and the negatively charged surfaces, contact activation is a rather difficult to control process. Hence, calibration of blood coagulation assays of the state of the art is a challenging task. The specific interaction with the relevant contact activation domain that allows for a defined stoichiometric activation of FXII leads to controlled activation of FXII and its downstream targets which can be leveraged to arrive at improved tests with superior reliability.

Moreover, the binding molecule of the invention can be used to calibrate the blood coagulation assays of the state of the art. Hence, the invention encompasses the use of the binding molecule as described herein, in particular the antibody as described herein, for calibrating in vitro blood coagulation tests. This means, that a defined coagulation activation induced by addition of defined amounts of the FXII activating antibodies is used as standard to assess coagulation activity induced by increasing concentrations of other FXII contact activators or other coagulation activator. The resulting clotting time or thrombin formation induced by the FXII activating antibody or the other coagulation activator, respectively, is measured, compared to each other and adjusted to each other. Therefore, blood coagulation tests can be calibrated by using an antibody as defined herein.

"Plasma" or "blood plasma" or "platelet poor plasma" (PPP) refers to the liquid portion of the blood from which the cells are separated (e.g. by centrifugation). In contrast to serum, plasma contains the blood clotting factors.

In the blood coagulation test citrate plasma, also named citrated plasma, is used. That means that the plasma is treated with sodium citrate in order to prevent blood clotting. Citrated plasma is used in order to prevent blood clotting before the onset of the blood clotting test.

Accordingly, another aspect of the invention refers to a method for activating FXII, comprising contacting FXII comprising sample with the binding molecule as defined herein.

The FXII comprising sample may be for example, blood or blood plasma. Preferably, the FXII comprising sample may be plasma, preferably citrated plasma.

FXII may further be contacted with polyphosphate.

The invention further relates to a kit comprising:
- binding molecule, preferably the antibodies as defined herein
- buffer
- further contact activator, such as polyphosphate,
- sodium citrate,
- phospholipids
- coagulation inhibitors such as heparin
- chromogenic substrate
- FXIIa,
- instructions for use.

The kit may further comprise sodium citrate and/or heparin.

Experiments

Examples

Identification of the Binding Site to Negatively Charged Surface of FXII which Mediates Contact Activation in the C-Terminal Part of the Proline Rich Domain of Native FXII (Human FXII Accession Number: P00748)

In order to determine the relevance of the non-catalytic domains of FXII for contact activation, clotting activities of 19 FXII deletion mutants (FIG. 1) were studied and compared to the activity of native FXII. Clotting times (FIG. 2) and thrombin generation (FIG. 3) triggered by kaolin of FXII deficient plasma reconstituted with recombinant full-length FXII (FXII_wt) or all FXII deletion mutants was similar to FXII-deficient plasma reconstituted with purified human FXII, except for FXII deficient plasma reconstituted with the FXII mutant lacking the full proline-rich domain, mutant FXII_ΔHC (in which the sequence of SEQ ID NO: 1 [uniprot P00748 numbering: Pro298-Ser358] is deleted) or particularly the C-terminal part of the proline rich domain, mutants FXII_ΔPR2/PR3 (in which the sequence of SEQ ID NO: 2 [uniprot P00748 numbering: His312-Ser358] is deleted) and FXII_ΔPR3 (in which the sequence of SEQ ID NO: 3 [uniprot P00748 numbering: Gln334-Ser358] is deleted) with similar clotting time as buffer control or GFP cells supernatant (FIG. 2 and FIG. 3). These findings indicate that activation of FXII by binding to negatively charged surface is mediated via the proline-rich region, and specifically by the C-terminal part of the proline rich domain, bonding the heavy chain to the light chain.

Figure 4A:
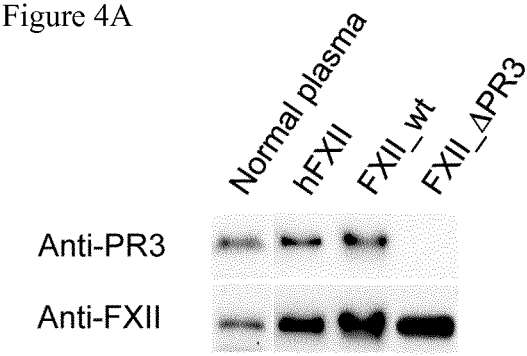
Figure 4B:
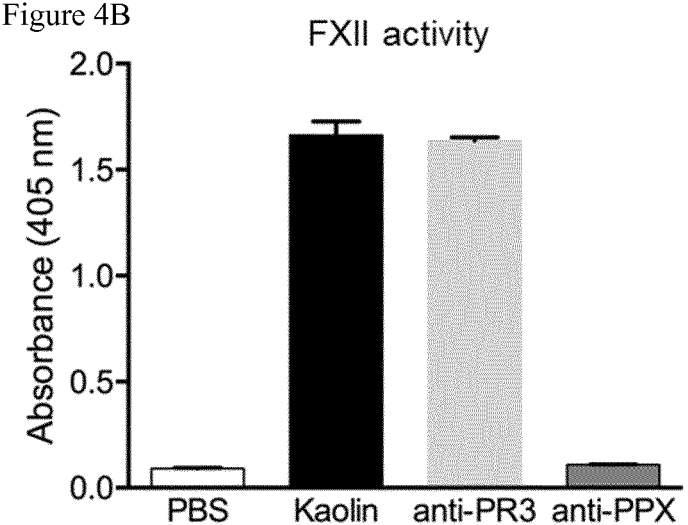
Figure 4C:
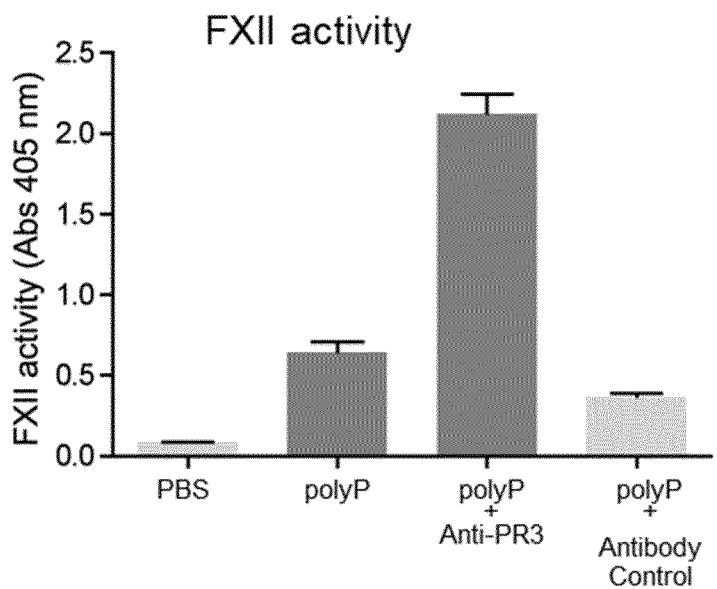
Figure 4D:
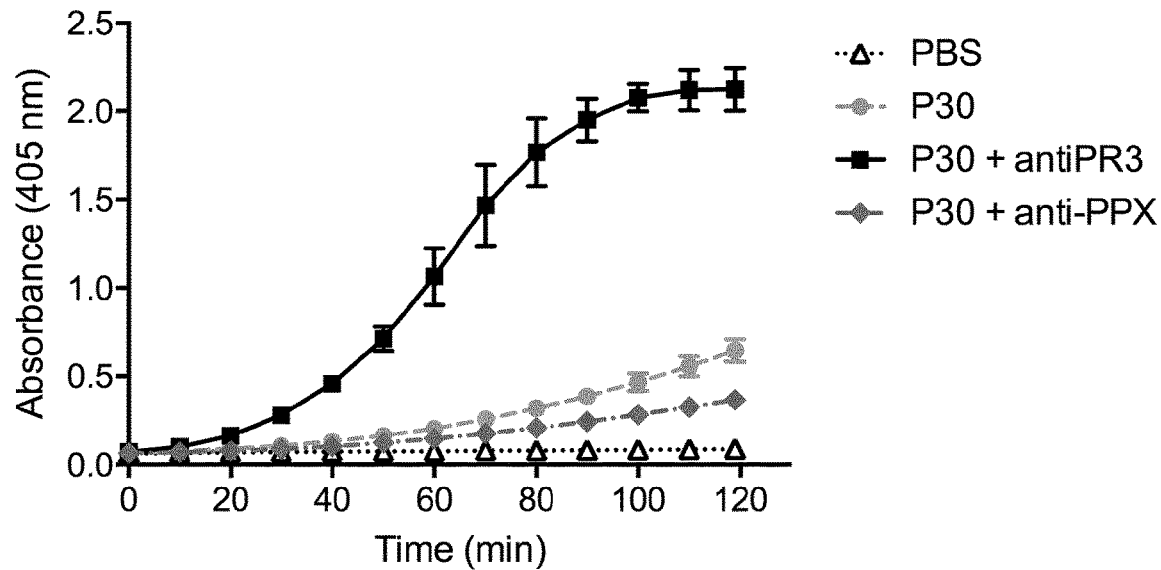
Figure 4E:
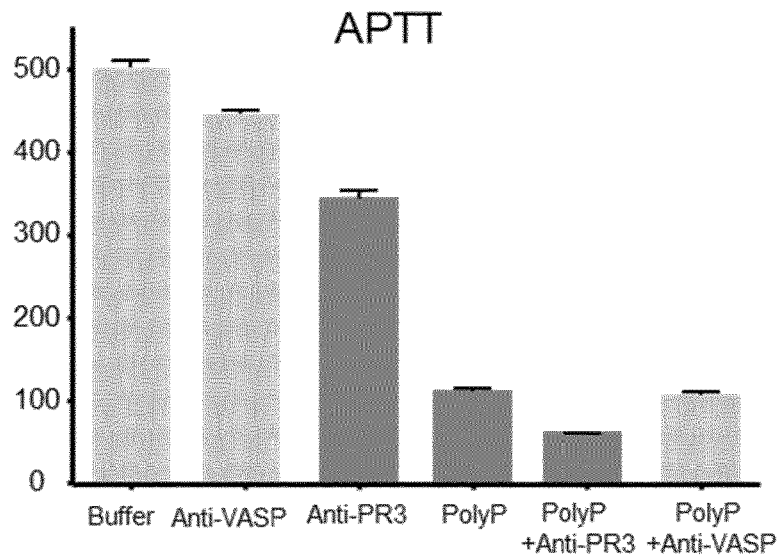
Figure 4F:
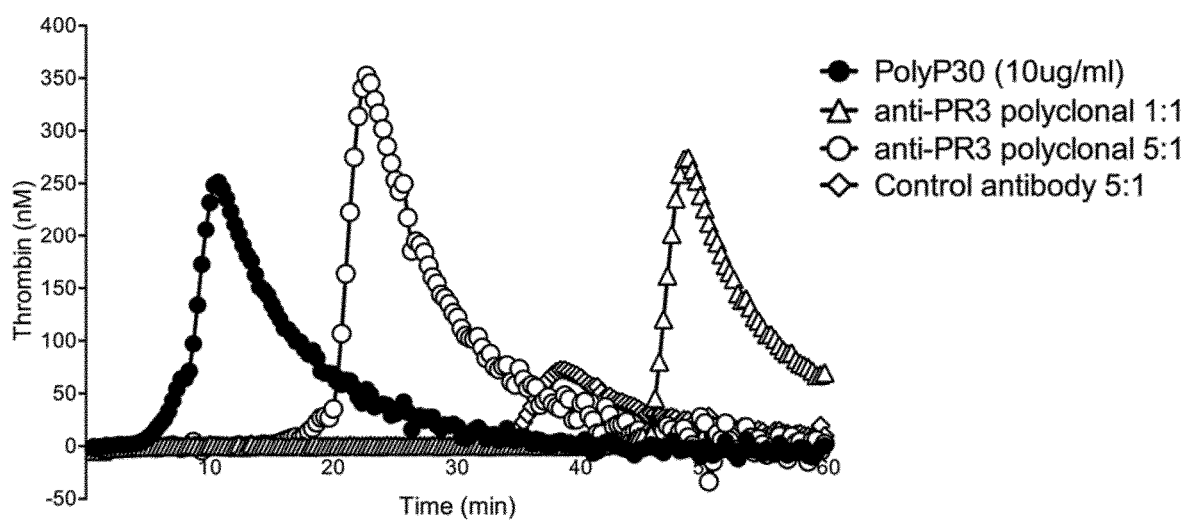

Antibody Anti-PR3 Directed against the Third Part of Proline Rich Domain (PR3) Induces FXII-Mediated Coagulation in Plasma A polyclonal antibody directed against the third part of proline-rich domain was generated by immunisation of rabbits with a 14 amino acid peptide (C-Gly-Ala-Leu-Pro-Ala-Lys-Arg-Glu-Gln-Pro-Pro-Ser-Leu-Thr; SEQ ID NO: 4) corresponding to amino acids 339 to 352 of FXII zymogen (Uniprot: P00748). Immunodetection analysis showed that the resulting antibody anti-PR3 appears to be specific in recognition of the C-terminal part of the proline-rich domain of FXII as it only detects native FXII but not recombinant expressed FXII mutant FXII_ΔPR3, contrary to commercial anti-FXII polyclonal antibody (FIG. 4A). After incubation with purified human FXII, anti-PR3 induces its activation (FIG. 4B) and it promotes polyphosphate-induced FXII-contact activation in a dose-dependent manner (FIG. 4C).

Figure 5A:
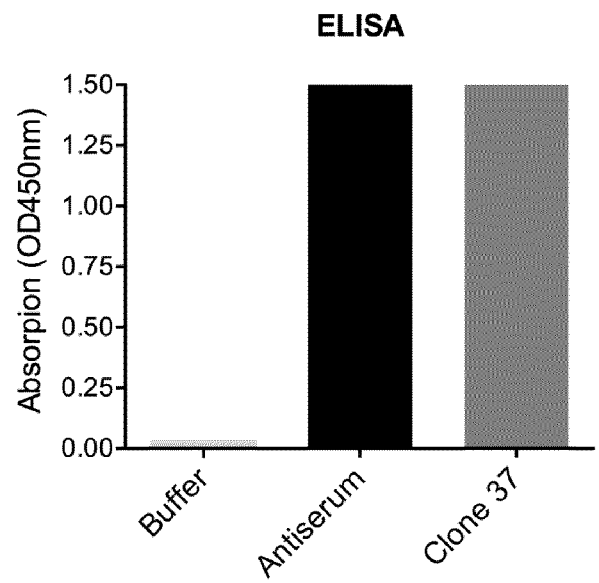
Figure 5B:
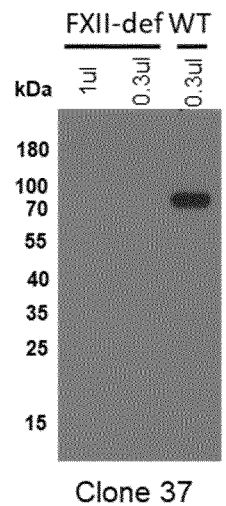
Figure 5C:
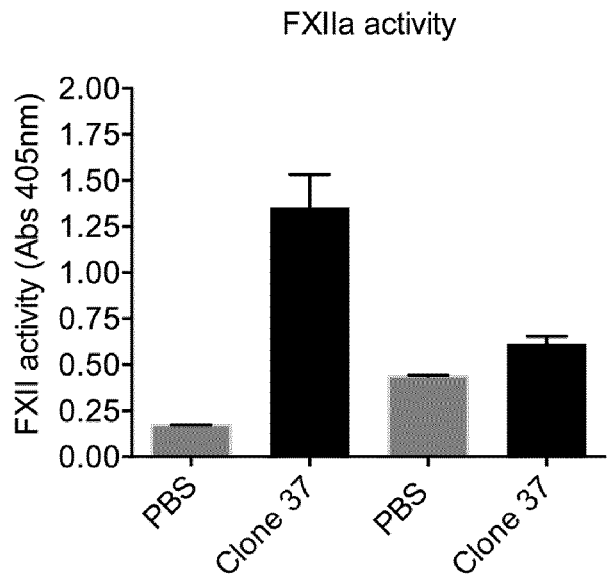
Figure 5D:
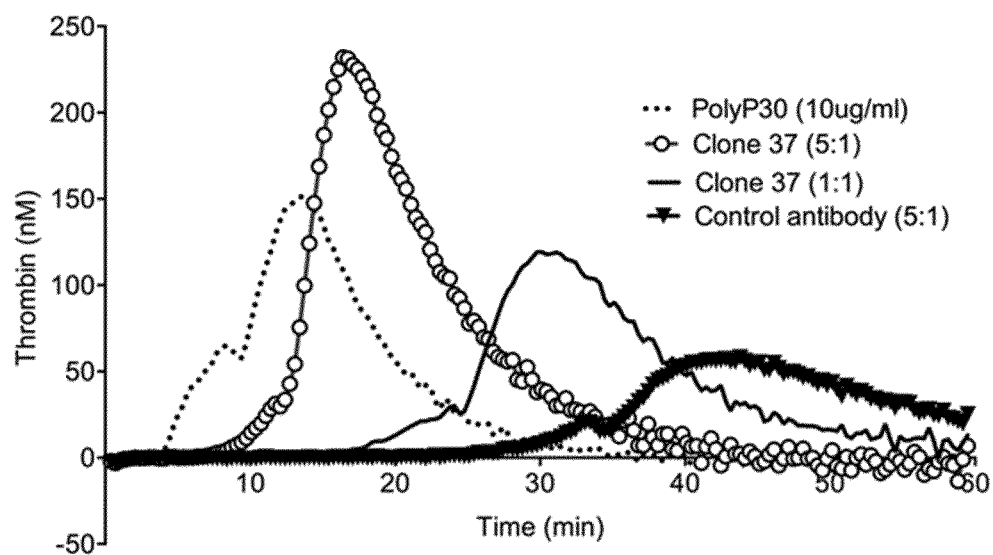

Antibody Clone HFXII 37-4-1 Directed against the C-Terminal Portion of the Proline Rich Domain Promotes Activates FXIII and Induces Plasma Coagulation A monoclonal antibody directed against the third part of proline-rich domain was generated by immunisation of mice with a 14 amino acid peptide (C-Gly-Ala-Leu-Pro-Ala-Lys-Arg-Glu-Gln-Pro-Pro-Ser-Leu-Thr; SEQ ID NO: 4) corresponding to amino acids 339 to 352 of FXII zymogen (Uniprot: P00748) and by fusion of mouse 5P2/0-Ag14 myeloma cells with spleen cells from immunized BLAB/c mouse. Analysis by ELISA and immunoblotting showed that the resulting clone 37 appears to be specific in recognition the 70 kDa FXII (FIG. 5A, 5B). After incubation with pooled human plasma, antibody purified from hybridoma HFXII 37-4-1 (clone 37) induces FXII activity (FIG. 5C) and it promotes polyphosphate-induced FXII-contact activation in a dose-dependent manner (FIG. 5D).

Hybridoma clone HFXII 37-4-1 was deposited with the DSMZ (Leibniz-Institut DSMZ—Deutsche Sammlung von Mikroorganismen and Zellkulturen GmbH, Inhoffenstr. 7 B, 38124 Braunschweig, Germany) on 27 Jun. 2018.

Material and Methods

FXII deletion mutants. FXII deletion mutants of full or part of the domains were engineered by insertion of restriction sites, digestion and religation of the FXII cDNA into pcDNA3 vector. Protein expression was obtain by transient transfection of different constructs into mammalian HEK293T cells. Results are shown in FIG. 1.

Clotting assay of human FXII deficient plasma reconstituted with FXII-wt or deletion mutants. Activated partial thromboplastin time (aPTT) was determined on a Blood Coagulation System (BCS) by adding FXII deficient plasma reconstituted with full length FXII (FXII_wt) or FXII deletion mutants from concentrated supernatant of cells to Pathromtin SL (Siemens HealthCare Diagnostics Products GmbH). As controls, FXII deficient plasma was reconstituted with purified human FXII from plasma (hFXII, Molecular innovations, USA) (positive control) or supernatant from cell transfected with GFP or PBS buffer (negative controls). For results see FIG. 2.

Thrombin formation in human FXII deficient plasma reconstituted with FXII_wt or deletion mutants. Endogenous Thrombin potential (ETP) in real time was analysed with the calibrated automated thrombography method using a Fluoroscan Ascent fluorometer (Thermo Scientific) equipped with a dispenser (Thrombinoscope BV). Coagulation was stimulated by adding kaolin to FXII deficient plasma reconstituted with full length FXII (FXII_wt) or FXII deletion mutants from concentrated supernatant of cells, in presence of phospholipids (Thrombinoscope BV), calcium and a fluorogenic substrate (ZGGR-AMC, Thrombinoscope BV). Thrombin formation was quantified using the Thrombinoscope software package (Version 3.0.0.29). As controls, FXII deficient plasma was reconstituted with purified human FXII (hFXII, Molecular innovations, USA) (positive control) or supernatant from cell transfected with GFP or PBS buffer (negative controls). Results are shown in FIG. 3.

Western blot. Anti-PR3 recognizes specifically the C-terminal part of the proline rich domain. Normal plasma, purified FXII (hFXII), full-length FXII (FXII_wt) and FXII mutant FXII_ΔPR3 (ΔGln$^{315}$-Ser$^{339}$) were loaded on SDS-PAGE gel and analysed by Western blotting using a goat polyclonal antibody anti-FXII (Anti-FXII, Nordic Biosite) or our rabbit antibody anti-PR3. Results are shown in FIG.

4A. FXII-deficient plasma as well as normal human pool plasma were loaded on SDS-PAGE gel and analysed by Western blotting using the antibody secreted by HFXII 37-4-1. Antibody secreted by HFXII 37-4-1 detected FXII at 70 kDa. Results are shown in FIG. 5B.

Enzymatic activation test. Antibody anti-PR3 activates human FXII. Anti-PR3 was incubated (2 h to 24 h) with purified FXII (hFXII) and the development of the enzymatic activity was analysed with chromogenic substrate S-2302 (Chromogenix, Sweden) in Multiskan™ GO Microplate reader (Thermo Scientific). As controls, hFXII was incubated with kaolin (positive control of contact activation, Ctrl.+) or with an antibody directed against a bacterial protein unrelated to plasma proteins (negative control for effect specificity to FXII, anti-PPX, Ctrl.−). For results see FIG. 4B.

Enzymatic activation test with antibody anti-PR3 and polyphosphate. Antibody anti-PR3 enhances FXII contact activation by the FXII natural activator polyphosphate. After pre-incubation of purified FXII (hFXII) with anti-PR3, the activator long chain polyphosphate (P30) was added and its enzymatic activity was analysed with the substrate S-2302 in Multiskan™ GO Microplate reader (Thermo Scientific). As negative control, hFXII was pre-incubated with anti-PPX antibody.

Real-Time Thrombin Generation Analysis

Thrombin formation in real-time was analyzed with the calibrated automated thrombography (CAT) method using a Fluoroscan Ascent fluorometer (Thermo Scientific, Waltham, MA, USA) equipped with a dispenser (Thrombinoscope BV, Maastricht, The Netherlands), as described by (Larsson et al., 2014). Briefly, thrombin generation was stimulated in 40 µl citrate-anticoagulated pooled normal plasma from healthy individuals (end concentration of 150 nM FXII) and 40 µl of PBS containing PolyP30 (10 µg/ml) or different antibodies. The antibodies used were the polyclonal antibody against the proline-rich 3 domain of FXII (anti-PR3), monoclonal antibodies against the proline-rich 3 domain of FXII (clone 37), F1 antibody (Nuijens et al., 1989), and a control antibody directed against double strand DNA dsDNA (non-existent in plasma). Antibodies were supplemented with PBS to reach an end concentration as indicated in the corresponding figures (e.g., 5:1 is the molar ratio of antibody: FXII in the reaction mixture). To start the reaction, the plasma mixture was complemented to a total volume of 120 µl with 20 µM phospholipids (20 µl) and 16.6 mM $Ca^{2+}$ and 2.5 mM fluorogenic substrate (20 µl, ZGGR-AMC, Thrombinoscope BV). Thrombin formation was quantified using the Thrombinoscope software package (Version 3.0.0.29).

Recalcification Time Plasma Clotting Assays

Recalcification times to assess plasma clotting were measured using a 'Kugelkoagulometer' (MC10 Plus, ABW Medizin and Technik GmbH, Lemgo, Germany) in 50 µl citrate-anticoagulated pooled normal plasma (end concentration of 150 nM FXII) preincubated with 25 µl phospholipids (40 µg/ml) and 25 µl of PBS containing F1 or dsDNA control antibody (750 nM) or Kaolin (100 µg/ml) for 175s at 37° C. Subsequently, the plasma samples were recalcified with 50 µl of a 25 mM calcium chloride solution. Phospholipids were isolated from Pathromtin SL reagent (Siemens Healthcare, Marburg, Germany) via centrifugation (14,000 rcf, 5 minutes) to discard silica as FXII activator.

REFERENCES

Citarella, F., Aiuti, A., La Porta, C., Russo, G., Pietropaolo, C., Rinaldi, M., and Fantoni, A. (1992). Control of human coagulation by recombinant serine proteases. Blood clotting is activated by recombinant factor XII deleted of five regulatory domains. Eur J Biochem 208, 23-30.

Citarella, F., Rayon, D. M., Pascucci, B., Felici, A., Fantoni, A., and Hack, C. E. (1996). Structure/function analysis of human factor XII using recombinant deletion mutants. Evidence for an additional region involved in the binding to negatively charged surfaces. Eur J Biochem 238, 240-249.

Clarke, B. J., Cote, H. C., Cool, D. E., Clark-Lewis, I., Saito, H., Pixley, R. A., Colman, R. W., and MacGillivray, R. T. (1989). Mapping of a putative surface-binding site of human coagulation factor XII. J Biol Chem 264, 11497-11502.

Larsson, M., Rayzman, V., Nolte, M. W., Nickel, K. F., Björkqvist, J., Jämsä, A., Hardy, M. P., Fries, M., Schmidbauer, S., Hedenqvist, P., Broomé, M., Pragst, I., Dickneite, G., Wilson, M. J., Nash, A. D., Panousis, C., Renné, T. (2014). A factor XIIa inhibitory antibody provides thromboprotection in extracorporeal circulation without increasing bleeding risk. Sci Transl Med 222, 222ra17.

Nuijens, J. H., Huijbregts, C. C., Eerenberg-Belmer, A. J., Meijers, J. C., Bouma, B. N., and Hack, C. E. (1989). Activation of the contact system of coagulation by a monoclonal antibody directed against a neodeterminant in the heavy chain region of human coagulation factor XII (Hageman factor). J Biol Chem 264, 12941-12949.

Pixley, R. A., Stumpo, L. G., Birkmeyer, K., Silver, L., and Colman, R. W. (1987). A monoclonal antibody recognizing an icosapeptide sequence in the heavy chain of human factor XII inhibits surface-catalyzed activation. J Biol Chem 262, 10140-10145.

Rayon, D. M., Citarella, F., Lubbers, Y. T., Pascucci, B., and Hack, C. E. (1995). Monoclonal antibody F1 binds to the kringle domain of factor XII and induces enhanced susceptibility for cleavage by kallikrein. Blood 86, 4134-4143.

Saito, H., Ishihara, T., Suzuki, H., and Watanabe, T. (1985). Production and characterization of a murine monoclonal antibody against a heavy chain of Hageman factor (factor XII). Blood 65, 1263-1268.

Vazquez-Lombardi R. et. al (2015) Challenges and opportunities for non-antibody scaffold drugs, Drug Discovery Today 20(10), 1271-1283

The invention claimed is:

1. An antibody or an antigen binding fragment thereof having the CDRs that share 100% sequence identity to the amino acid sequences of the CDRs of the monoclonal antibody produced from the hybridoma deposited with the Leibniz-Institute Deutsche Sammlung von Mikroorganismen und Zellkulturen having the DSMZ designation 37-4-1.

2. A monoclonal antibody produced from the hybridoma deposited with the Leibniz-Institute Deutsche Sammlung von Mikroorganismen und Zellkulturen having the DSMZ designation HFXII 37-4-1.

* * * * *

SEQUENCE LISTING

<160> NUMBER OF SEQ ID NOS: 4

<210> SEQ ID NO 1
<211> LENGTH: 61
<212> TYPE: PRT
<213> ORGANISM: Homo sapiens

<400> SEQUENCE: 1

```
Pro Thr Gln Ala Ala Pro Pro Thr Pro Val Ser Pro Arg Leu His Val
1               5                   10                  15

Pro Leu Met Pro Ala Gln Pro Ala Pro Pro Lys Pro Gln Pro Thr Thr
            20                  25                  30

Arg Thr Pro Pro Gln Ser Gln Thr Pro Gly Ala Leu Pro Ala Lys Arg
        35                  40                  45

Glu Gln Pro Pro Ser Leu Thr Arg Asn Gly Pro Leu Ser
    50                  55                  60

<210> SEQ ID NO 2
<211> LENGTH: 47
<212> TYPE: PRT
<213> ORGANISM: Homo sapiens

<400> SEQUENCE: 2

His Val Pro Leu Met Pro Ala Gln Pro Ala Pro Pro Lys Pro Gln Pro
1               5                   10                  15

Thr Thr Arg Thr Pro Pro Gln Ser Gln Thr Pro Gly Ala Leu Pro Ala
            20                  25                  30

Lys Arg Glu Gln Pro Pro Ser Leu Thr Arg Asn Gly Pro Leu Ser
        35                  40                  45

<210> SEQ ID NO 3
<211> LENGTH: 25
<212> TYPE: PRT
<213> ORGANISM: Homo sapiens

<400> SEQUENCE: 3

Gln Ser Gln Thr Pro Gly Ala Leu Pro Ala Lys Arg Glu Gln Pro Pro
1               5                   10                  15

Ser Leu Thr Arg Asn Gly Pro Leu Ser
            20                  25

<210> SEQ ID NO 4
<211> LENGTH: 14
<212> TYPE: PRT
<213> ORGANISM: Homo sapiens

<400> SEQUENCE: 4

Gly Ala Leu Pro Ala Lys Arg Glu Gln Pro Pro Ser Leu Thr
1               5                   10
```